United States Patent [19]
Hermanson

[11] Patent Number: 5,730,118
[45] Date of Patent: Mar. 24, 1998

[54] CARRIER FOR ASTHMA INHALER

[76] Inventor: Susan Thomas Hermanson, 840 Park Ave., New York, N.Y. 10021

[21] Appl. No.: 606,723

[22] Filed: Feb. 27, 1996

[51] Int. Cl.[6] ................................................. A61M 16/00
[52] U.S. Cl. ................................. 128/200.14; 128/205.22
[58] Field of Search .................... 128/200.14, 200.18, 128/200.21, 204.21, 204.23, 205.22

[56] References Cited

U.S. PATENT DOCUMENTS

| | | |
|---|---|---|
| 3,254,803 | 6/1966 | Meshberg . |
| 3,301,255 | 1/1967 | Thompson ........................ 128/200.21 |
| 3,302,834 | 2/1967 | Alsop . |
| 3,830,270 | 8/1974 | Hagert et al. ............................. 150/52 |
| 4,023,712 | 5/1977 | Bakiak et al. . |
| 4,106,698 | 8/1978 | Lin . |
| 4,257,415 | 3/1981 | Rubin ................................ 128/204.21 |
| 4,590,951 | 5/1986 | O'Connor ........................ 128/204.23 |
| 4,739,913 | 4/1988 | Moore ............................... 128/205.22 |
| 4,949,715 | 8/1990 | Brugger ............................ 128/204.21 |
| 5,088,624 | 2/1992 | Hackett et al. . |
| 5,111,968 | 5/1992 | Wilkerson . |
| 5,119,806 | 6/1992 | Palson et al. . |
| 5,226,563 | 7/1993 | Coggiola . |
| 5,299,565 | 4/1994 | Brown .............................. 128/200.14 |
| 5,400,934 | 3/1995 | Ducros ............................. 128/205.22 |

OTHER PUBLICATIONS

Pulmo–Aide Traveler Model 6610D, DeVilbiss Health Care, Inc. Somerset, PA (Advertisement), 1991.

*Primary Examiner*—Vincent Millin
*Assistant Examiner*—Robert N. Wieland
*Attorney, Agent, or Firm*—Fitzpatrick, Cella, Harper & Scinto

[57] ABSTRACT

A device for carrying a fluid dispensing unit includes a container for receiving the fluid dispensing unit and a chain connected to the container for carrying the container and retaining the dispensing unit in the container. The dispensing unit can be secured to the chain by sandwiching the chain between a cap and the dispensing unit itself.

19 Claims, 3 Drawing Sheets

CARRIER FOR ASTHMA INHALER

BACKGROUND OF THE INVENTION

1. Field of the Invention

The present invention relates generally to a holder or carrier for a device for dispensing fluids for nasal and/or oral inhalation. More particularly, the invention relates to a holder for an inhaler that can be suspended from a chain or necklace worn around a user's neck, with the chain not only carrying the holder, but also securing the inhaler within the holder.

2. Description of the Prior Art

Devices for dispensing fluids for nasal and/or oral inhalation, i.e., inhalers, are well-known. These inhalers are useful in administering a medicine or medicament in the form of an atomized fluid spray to patients suffering from bronchial conditions such as, for example, bronchial asthma. When an asthma attack occurs, it is desirable for the medicament to be inhaled directly by the patient. Typically, the medicament is dispersed by a propellant under pressure in a container which is actuated to eject an atomized spray or aerosol of the medicament. One such inhaler is described in U.S. Pat. No. 3,302,834 to Alsop.

However, since a user never knows when an asthma attack will occur, the inhaler must be accessible at all times. The inhaler can be carried in a pocket of the user's clothes or in a handbag, but if the user changes clothes or does not bring the handbag, the inhaler will not be readily accessible. Further, in the middle of an intense asthma attack it may be difficult to search through a pocket or handbag to find the inhaler.

It has been proposed in U.S. Pat. No. 4,106,698 to Lin to suspend a vaporizer around a user's neck with a chain. The chain is passed through an eyelet of a vaporizer housing. Although in one embodiment the vaporizer can accommodate a disposable refill cartridge, the housing cannot accommodate a standard asthma inhaler on the market. Further, if the vaporizer is damaged beyond repair, the entire vaporizer is useless and therefore it would not be practical to form the vaporizer of attractive materials that may be expensive or to provide the vaporizer with any ornamental features that may be expensive to create.

It has been proposed in U.S. Pat. No. 4,023,712 to Babiak, et al. to provide a portable spray container device including a pressurized container with a spray outlet, a covering cap for the pressurized container and a necklace chain attached through a wire loop in the cap. The device outputs a taste spray for inhibiting a person's appetite. However, the pressurized container must be removed from the cap suspended by the necklace whenever the device is to be used. Also, the necklace does not retain the container in the cap.

What is needed in the art is to provide a carrier for a fluid dispenser in which the chain not only carries the housing, but also retains the dispenser in the housing in order to minimize parts to simplify the design. Not only should the carrier be practical, but it can also be attractive. That is, the carrier should not only function to securely carry the dispenser in a simple yet effective manner, but it can also have an aesthetic appearance.

SUMMARY OF THE INVENTION

It is a principal object of the present invention to provide a carrier for an inhaler that can be worn by a user at all times.

Another object of the invention is to provide a carrier for an inhaler that can be worn around a user's neck such that the inhaler can be either taken out of the carrier and utilized or be utilized while retained in the carrier.

It is another object of the present invention to provide a carrier for an inhaler that has ornamental features as to also function as an attractive pendant.

Still another object of the present invention is to provide a carrier for an inhaler that is suspended from a user's neck by a chain, wherein the chain also functions to retain the inhaler within the carrier.

Yet another object of the present invention is to provide a carrier for an asthma inhaler that can be formed of either inexpensive or expensive materials.

A still further object of the present invention is to provide a carrier for an inhaler that can be manufactured and sold at a reasonable cost.

In one aspect of the present invention a device for spraying or dispensing a fluid comprises a container for receiving a fluid dispensing unit, and carrying means connected to the container for carrying the container and retaining the dispensing unit in the container.

In another aspect of the present invention a carrier for removably carrying a fluid dispensing unit for dispensing a fluid comprises a housing for receiving the dispensing unit, and a chain connected to the housing for carrying the housing. The chain also retains the dispensing unit in the housing.

In yet another aspect of the present invention a carrier for removably carrying a fluid dispensing unit includes a container for housing the dispensing unit, the container having an open end for receiving the dispensing unit, and carrying means connected to the container for carrying the housing. The carrying means is connected to the container at first and second locations and spans the open end of the container.

These and other objects, aspects, features and advantages of the present invention will become apparent from the following detailed description of the preferred embodiments taken in conjunction with the accompanying drawings.

DETAILED DESCRIPTION OF THE PREFERRED EMBODIMENTS

Figure 1:
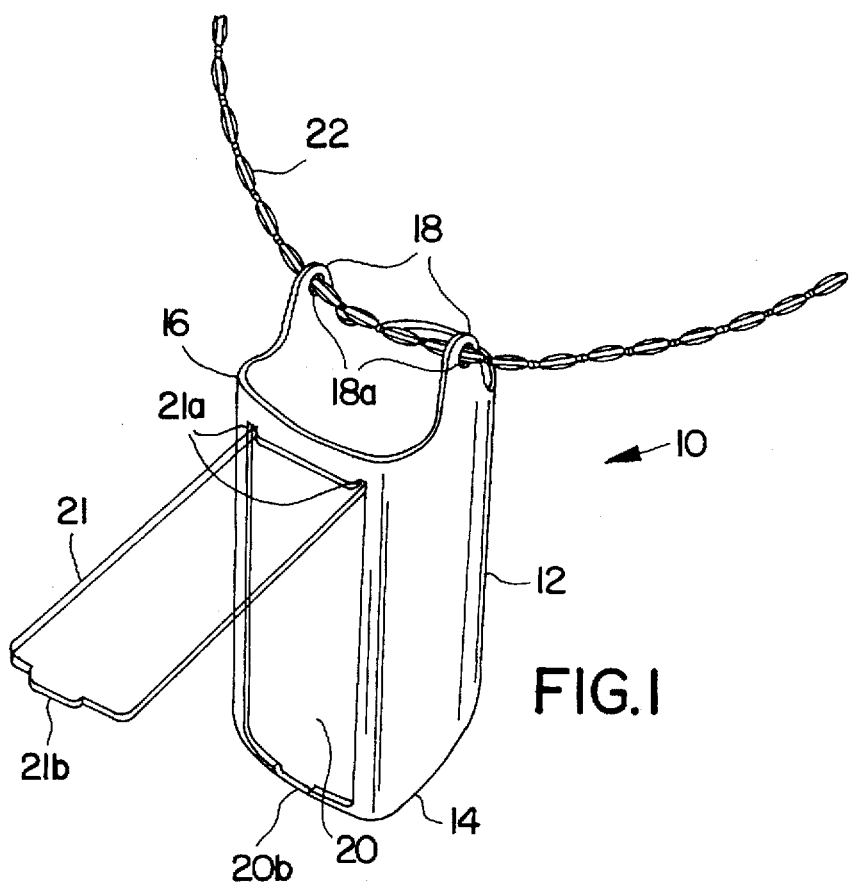
FIG. 1 is a perspective view of a carrier for an inhaler of the present invention.

Referring to FIG. 1, reference numeral 10 generally identifies the carrier for the inhaler of a first embodiment of the present invention. The carrier is comprised of a main housing or container 12 having a distal end 14 and a proximal end 16, as well as a necklace or chain 22. The proximal end 16 is always open, and the distal end 14 can be open or closed. The housing 12 is generally cylindrical and can be shaped, for example, with a flat face. The housing includes two lobes 18 disposed on the periphery of the open end 16. Each of the lobes 18 includes an eyelet 18a for receiving the chain 22. The diameter of each eyelet 18a is large enough so that the chain can freely pass through the eyelets.

The exterior of the housing 12 can be formed with any ornamental design so that it is aesthetically pleasing to a viewer. The housing 12 can be formed of a molded polymer, aluminum, brass or a precious metal. The necklace 22 can be in the form of a chain formed of any metal including precious metals, or can be formed of a leather or synthetic strap.

The housing 12 can optionally be provided with a recess 20 into which a clear cover 21 can fit. The cover 21 is hinged to the recess 20 with hinges 21a. Further, the cover 21 is provided with a detent 21b for snapping into a locking recess 20b in the housing 12. Printed information, such as the user's address, phone number, name of doctor, etc., can be placed in the recess 20 and held in place by the cover 21 so that the information can be readily available to anyone assisting the user.

Figure 4:
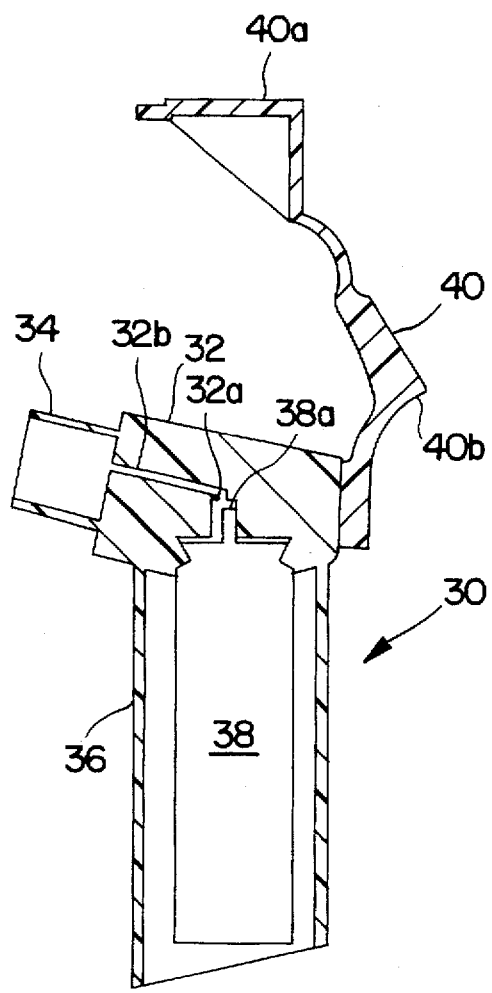
FIG. 4 is a cross-sectional view of a typical inhaler for use with the carrier of the present invention.

The proximal end 16 of the housing 12 is for receiving an inhaler. A typical inhaler 30 useable with the present invention is shown in FIG. 4. The inhaler is comprised of a head 32, mouthpiece 34 and body 36. A disposable cartridge 38, having a valve stem 38a is insertable into the body 36 of the inhaler and removeably secured to the inhaler by any suitable means, such as a friction fit. The valve stem 32a actuates an unshown release valve of the cartridge 38. When the cartridge 38 is loaded in the inhaler 30, the valve stem 38a is disposed within a bore 32a of the head 32. The bore 32a communicates with a passage 32b leading to the mouthpiece 34. With this arrangement, when the cartridge 38 is moved upwards relative to the head 32, the valve stem 38a abuts an end of the bore 32a to release the medicant and propellant. In operation, to receive a dose of the medicant, a user would place the mouthpiece 34 in the mouth, depress the cartridge 38 and inhale the ejected medicant.

To keep the passageways of the inhaler clean when not in use, a capping device 40 is used. The capping device 40 includes a cap 40a which snaps over the mouthpiece 34, and a flexible connector 40b for securing the cap to the head 32. This prevents the cap 40a from being lost when not in use. Alternatively, the flexible connector 40b can be integrally formed with the head 32.

The inhaler 30 can be formed of a molded polymer, and can be formed as one integral unit or can be an assembly of separate components.

The inner periphery of the housing 12 of the carrier 10 is dimensioned to be slightly larger than the outer periphery of the body 36 of the actuator 30. Also, the depth of the housing 12 from the proximal end 16 to the distal end 14 is dimensioned to be slightly longer than the height of the body 36 of the actuator 30. The periphery of the proximal end 16 of the housing 12 is shaped to be complementary to the bottom surface of the head 32 of the inhaler 30, with the head 32 having a larger dimension than the inner periphery of the housing 12 so as to support the inhaler 30 within the housing. Further, when the inhaler 30 is inserted in the carrier 10, the height of the eyelets 18 of the housing 12 is substantially equal to the height of the upper surface of the head 32 of the inhaler 30.

Figure 2:
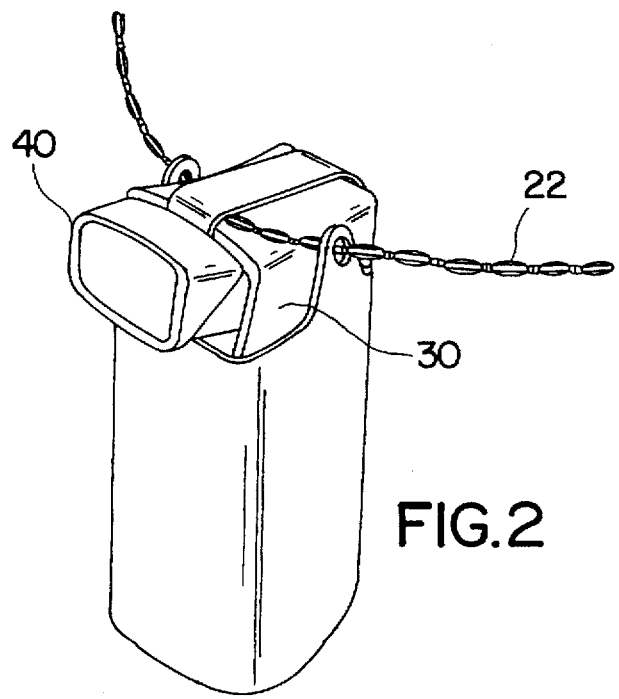
FIG. 2 is a perspective view of a carrier for an inhaler of the present invention with the inhaler having been loaded in the carrier and capped.

The manner of using the carrier of the present invention will now be described. To load the inhaler 30 into the carrier 10, the user will first uncap the cap 40a from the mouthpiece 34 of the inhaler 30. Then the chain 22 is pulled through the outlets 18 such that the chain does not obstruct the open, proximal end 16 of the housing 12. The inhaler 30 is then inserted into the proximal end 16 of the housing 12 until the bottom surface of the head 32 abuts the edge of the proximal end 16. The chain is tensioned so that it is positioned on or above the top of the head 32. The positioning of the chain 22 spanned between the eyelets 18 will prevent the inhaler 30 from falling out of the housing 12. Finally, the cap 40a is snapped onto the mouthpiece, thereby trapping the chain between the connector 40b and the top of the head 32 as best seen in FIG. 2.

With this arrangement, when the inhaler is not in use the chain is secured between the capping member 40 and the top of the head 32. Accordingly, even if the tension of the chain between the eyelets 18 relaxes, the inhaler 30 will remain affixed to the chain 32 and thus secured in the carrier.

When a user desires to use the inhaler, first the cap 40a is snapped off the mouthpiece 34. Then the chain 22 is pulled away from the proximal end 16 of the housing 12. The user then grasps the inhaler 30 and withdraws it from the carrier 10. The inhaler 30 can then be used in the usual manner. After use, the inhaler 30 can be replaced in the carrier 10 in the manner described previously.

Alternatively, if the distal end 14 of the carrier housing 12 is also open, the inhaler 30 need not be withdrawn from the carrier. Rather, after the inhaler is uncapped, the user's finger can be inserted through the open, distal end 14 to actuate the inhaler.

Figure 3:
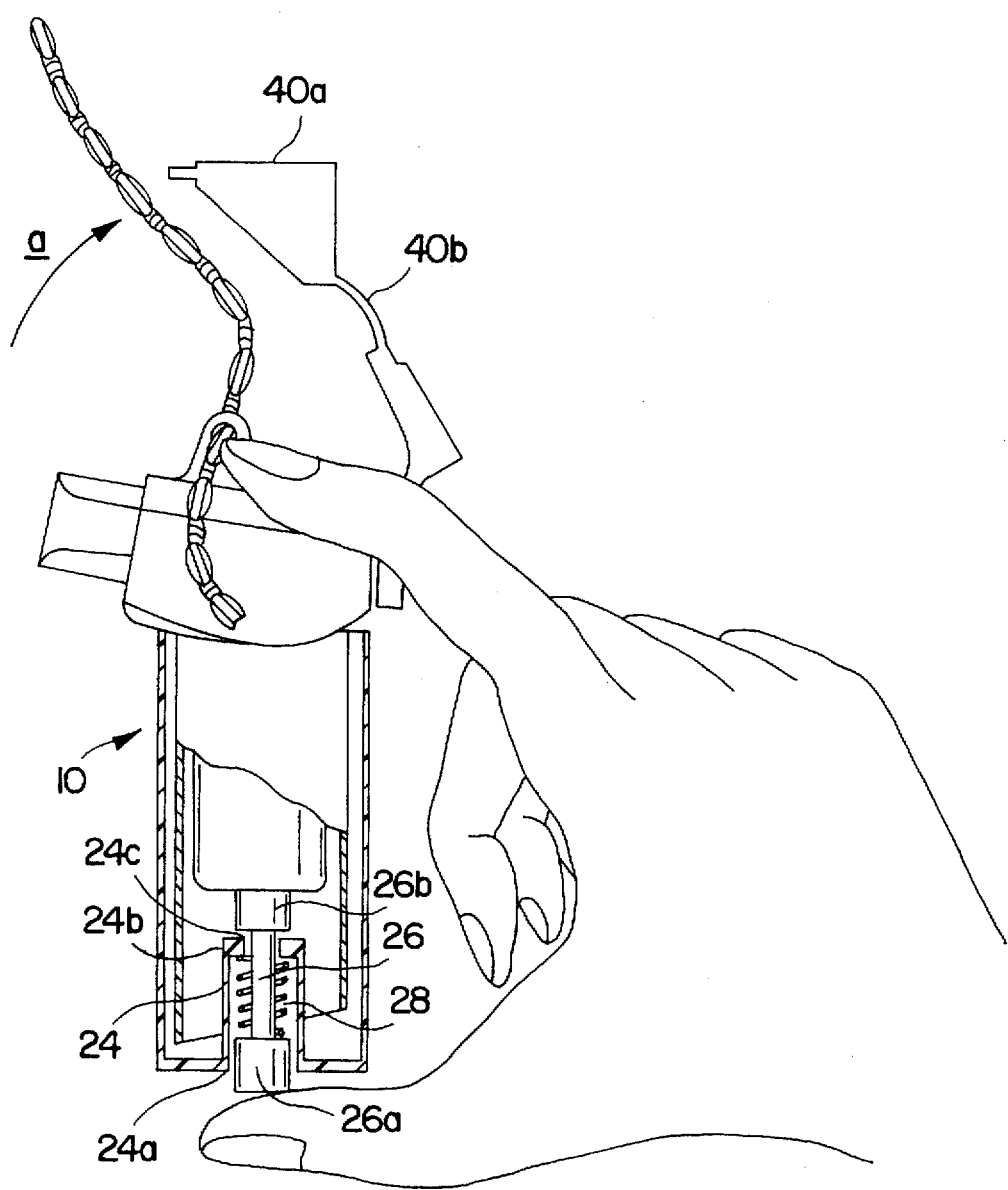
FIG. 3 is a partial cross-sectional view of a second embodiment of a carrier for an inhaler of the present invention with the inhaler loaded in the carrier.

A second embodiment of the inhaler carrier of the present invention will be described referring to FIG. 3. The carrier 10' of the second embodiment is similar to the carrier 10 of the first embodiment in many respects and like reference numerals will be used to designate like elements. The improvement of the second embodiment is that it utilizes an actuator to actuate the inhaler 30 without having to withdraw it from the housing 12 or having to insert the user's finger into the distal end 14.

The actuator is comprised of a recess 24 in the housing 12 having an open end 24a and a terminal end 24b with a through opening 24c. An actuator shaft 26 extends through the through opening 24c and projects outwardly of the bottom surface of the container 12. A compression spring 28 biases the actuator shaft 26 away from the terminal end 24b of the recess 24. A first end of the shaft 26 includes an actuator button 26a and the opposite end includes an abutment 26b. When the inhaler 30 is loaded in the carrier 10', the abutment 26b abuts against a bottom surface of the cartridge 38 of the inhaler 30. When the actuator 26a is depressed against the biasing force of the spring 28, the actuator shaft 26 forces the abutment 26b to urge the cartridge 38 toward the head 32 to discharge the medicant and the propellant in the normal manner. Thus, a user need not withdraw the inhaler 30 from the carrier 10 when needed. Rather, the user only has to snap the cap 40a off the mouthpiece 34, place the mouthpiece 34 in the mouth, depress the actuator button 26a and inhale. Loading and unloading of the inhaler 30 is identical to that in the first embodiment.

The present invention is not to be limited to a pendant or necklace for wearing around a patient's neck. For example, the present invention is also applicable to use as a bracelet or other means for adorning a person.

Although specific embodiments of the present invention have been described above in detail, it will be understood that this description is merely for purposes of illustration. Various modifications of and equivalent structures corresponding to the disclosed aspects of the preferred embodiments in addition to those described above may be made by those skilled in the art without departing from the spirit of the present invention which is defined in the following claims the scope of which is to be accorded the broadest interpretation so as to encompass such modifications and equivalent structures.

I claim:

1. A device for holding a dispensing unit for spraying or dispensing a fluid, said device comprising:

a container for receiving the fluid dispensing unit; and carrying means connected to said container for carrying said container and retaining said dispensing unit in said container.

2. A device according to claim 1, wherein said container is of a generally cylindrical shape having a first, open end through which said fluid dispensing unit is received, and a second end.

3. A device according to claim 2, wherein said container comprises a pair of eyelets disposed adjacent the first end for slidably receiving said carrying means.

4. A device according to claim 3, wherein a portion of said carrying means spanning said pair of eyelets contacts a surface of the dispensing unit received in said container to retain the dispensing unit in said container.

5. A device according to claim 4, further comprising the dispensing unit, wherein said dispensing unit includes a dispensing head having a mouthpiece and a cap member attached by a connecting member for capping said mouthpiece, wherein said portion of said carrying means is secured between said connecting member and said dispensing head when said cap member caps said mouthpiece.

6. A device according to claim 5, wherein said container further comprises an actuator moveably disposed in the second end of said container for discharging the fluid in said dispensing unit.

7. A device according to claim 1, wherein the fluid comprises an asthma inhalant.

8. A carrier for removably carrying a fluid dispensing unit for dispensing a fluid, said carrier comprising:

a housing for receiving the dispensing unit; and a chain connected to said housing for carrying said housing, said chain being disposed to retain the dispensing unit in said housing.

9. A carrier according to claim 8, wherein said housing is of a generally cylindrical shape having a first, open end, through which the fluid dispensing unit is received, and a second end.

10. A carrier according to claim 8, wherein said housing comprises a pair of eyelets disposed adjacent the open end for slidably receiving said chain.

11. A carrier according to claim 10, wherein a portion of said chain spanning said pair of eyelets contacts a surface of the dispensing unit received in said housing to retain the dispensing unit in said housing.

12. A carrier according to claim 11, further comprising the dispensing unit, wherein the dispensing unit includes a dispensing head having a mouthpiece and a cap member attached by a connecting member for capping the mouthpiece, and wherein said portion of said chain is secured between the connecting member and the dispensing head when the cap member caps the mouthpiece.

13. A carrier according to claim 12, wherein said housing further comprises an actuator moveably disposed in the second end of said housing for discharging the fluid in the dispensing unit.

14. A container according to claim 8, wherein the fluid comprises an asthma inhalant.

15. A carrier for removably carrying a fluid dispensing unit, said carrier comprising:

a container for housing the dispensing unit, said container having an open end for receiving the dispensing unit; and carrying means connected to said container for carrying said container, with said carrying means connected to said container at first and second locations and spanning the open end of said container.

16. A device according to claim 15, wherein the first and second locations comprise a pair of eyelets disposed adjacent the open end for slidably receiving said carrying means.

17. A device according to claim 16, wherein a portion of said carrying means spanning said pair of eyelets contacts a surface of the dispensing unit to retain the dispensing unit in said container.

18. A device according to claim 15, wherein said container further comprises an actuator moveably disposed in an end opposite the open end of said container for discharging the fluid in the dispensing unit.

19. A device according to claim 15, wherein the fluid comprises an asthma inhalant.

* * * * *